US00PP20642P2

(12) United States Plant Patent
Wright

(10) Patent No.: US PP20,642 P2
(45) Date of Patent: Jan. 12, 2010

(54) BLUEBERRY PLANT NAMED 'C97-390'

(50) Latin Name: ***Vaccinium* hybrid**
Varietal Denomination: C97-390

(75) Inventor: Gary Wright, Corindi Beach (AU)

(73) Assignee: Costaexchange Limited, New South Wales (AU)

( * ) Notice: Subject to any disclaimer, the term of this patent is extended or adjusted under 35 U.S.C. 154(b) by 0 days.

(21) Appl. No.: 12/228,523

(22) Filed: Aug. 12, 2008

(51) Int. Cl.
*A01H 5/00* (2006.01)

(52) U.S. Cl. ..... Plt./157

(58) Field of Classification Search ..... Plt./157
See application file for complete search history.

*Primary Examiner*—Annette H Para
(74) *Attorney, Agent, or Firm*—Ballew Law

(57) ABSTRACT

A new and distinct cultivar of blueberry (*Vaccinium* hybrid) plant named 'C97-390', characterized by its combination of upright to bushy plant shape and strong plant growth vigor, evergreen foliage, earliness of flowering and fruiting, large fruit size, firm fruit suited to handling, attractive dark blue fruit color and small picking scar. This combination results in higher quality fruit with an earlier availability than other varieties.

3 Drawing Sheets

Latin name of genus and species of plant claimed: *Vaccinium* hybrid.

Variety denomination: 'C97-390'.

BACKGROUND OF THE INVENTION

The present invention relates to a new and distinct perennial variety of *Vaccinium* hybrid (Southern Highbush Blueberry), which has been given the variety denomination of 'C97-390'. Its market class is that of a fruiting plant. 'C97-390' is intended for use as fresh fruit for shipping, customer pick and processing markets and as a home garden plant.

The new *Vaccinium* hybrid cultivar is a selection resulting from seedlings produced in a controlled breeding programme of *Vaccinium* at Gainesville, Fla., USA in 1994 from a cross of seed parent 'F92-84' (unpatented) and pollen parent 'F95-54' (unpatented). The new cultivar was discovered and selected as a single plant within a population of plants of *Vaccinium* hybrids in 1997 in a commercial field plantation environment at Corindi Beach, New South Wales, Australia. Selection criteria was a combination of upright to bushy plant shape and strong plant growth vigor, evergreen foliage, earliness of flowering and fruiting, large fruit size, firm fruit suited to handling, attractive dark blue fruit color and small picking scar. The selection was subsequently evaluated for a number of years at the commercial farms of BerryExchange at Corindi Beach, New South Wales, Australia.

Asexual reproduction of the new cultivar by cutting propagation since 1997 at Corindi Beach, New South Wales, Australia and has demonstrated that the new cultivar reproduces true to type with all of the characteristics, as herein described, firmly fixed and retained through successive generations of such asexual propagation.

The new variety has been primarily compared to the variety 'Sharpe Blue' (unpatented). In Corindi Beach, New South Wales, Australia the time of fruit ripening of 'C97-390' is classified as very early to early whereas the time of fruit ripening of 'Sharpe Blue' is classified as 'mid-season'. The earlier time of fruit ripening of 'C97-390' allows for a greater period of production on farm and an ability to supply fresh fruit markets at an earlier date than 'Sharpe Blue'. The time of vegetative bud burst of 'C97-390' is 'late' whereas the time of vegetative bud burst of 'Sharpe Blue' is 'early to mid-season'. The time of beginning of flowering of 'C97-390' is classified as 'very early to early' whereas the time of beginning of flowering of time of 'Sharpe Blue' is classified as 'early to mid-season'. The time of fruit ripening of 'C97-390' is classified as 'very early to early' whereas 'Sharpe Blue' is classified as 'mid-season'. Therefore one of the attributes of the new variety is that it has vegetative bud burst later than 'Sharpe Blue', yet it flowers and ripens earlier than 'Sharpe Blue'. The plant growth habit of 'C97-390' is 'upright to bushy' whereas the plant growth habit of 'Sharpe Blue' is 'bushy to spreading'. The leaf width of 'C97-390' is 'medium' (25–30 mm) whereas the leaf width of 'Sharpe Blue' is 'broad' (40–45 mm). The berry color of 'C97-390' is a dark blue whereas the berry color of 'Sharpe Blue' is a lighter blue. The berry firmness of 'C97-390' is firm whereas 'Sharpe Blue' is soft. The picking scar of 'C97-390' is classified as 'dry' whereas the picking scar of 'Sharpe Blue' is 'wet'. This combination of fruiting attributes results in 'C97-390' being a more suitable variety for commercial handling including picking and packing than 'Sharpe Blue'.

SUMMARY OF THE INVENTION

The following characteristics of the new cultivar have been repeatedly observed and can be used to distinguish 'C97-390' as a new and distinct cultivar of *Vaccinium* hybrid plant:

1. Upright to bushy plant growth habit
2. Late timing of vegetative bud burst
3. Very early to early timing of beginning of flowering
4. Very early to early timing of fruit ripening
5. Dark blue berry color
6. Berry firmness is firm
7. Picking scar is dry Plants of the new cultivar differ from plants of the *Vaccinium* hybrid parents primarily in very early to early timing of beginning of flowering and very early to early timing of fruit ripening whereas the parent varieties are early to mid season in these characters.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'C97-390'.

DETAILED BOTANICAL DESCRIPTION

Figure 1:
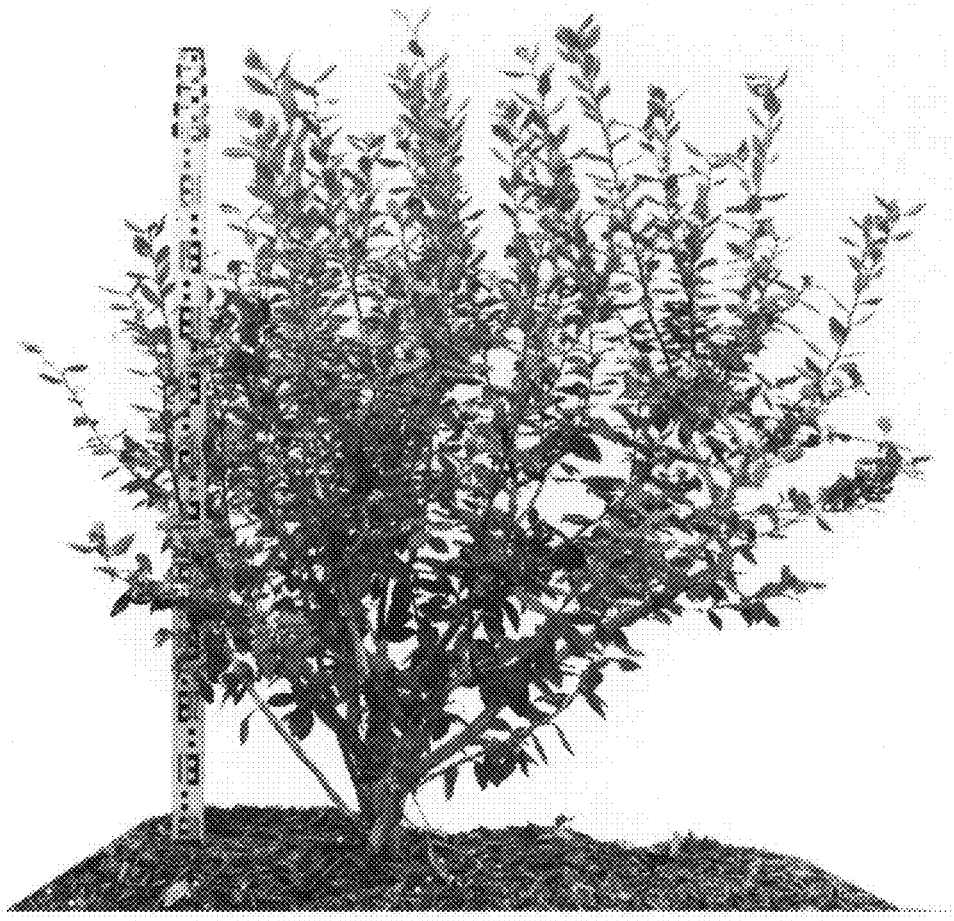
FIG. 1 illustrates a 'C97-390' in a commercial field planting.
Figure 2:
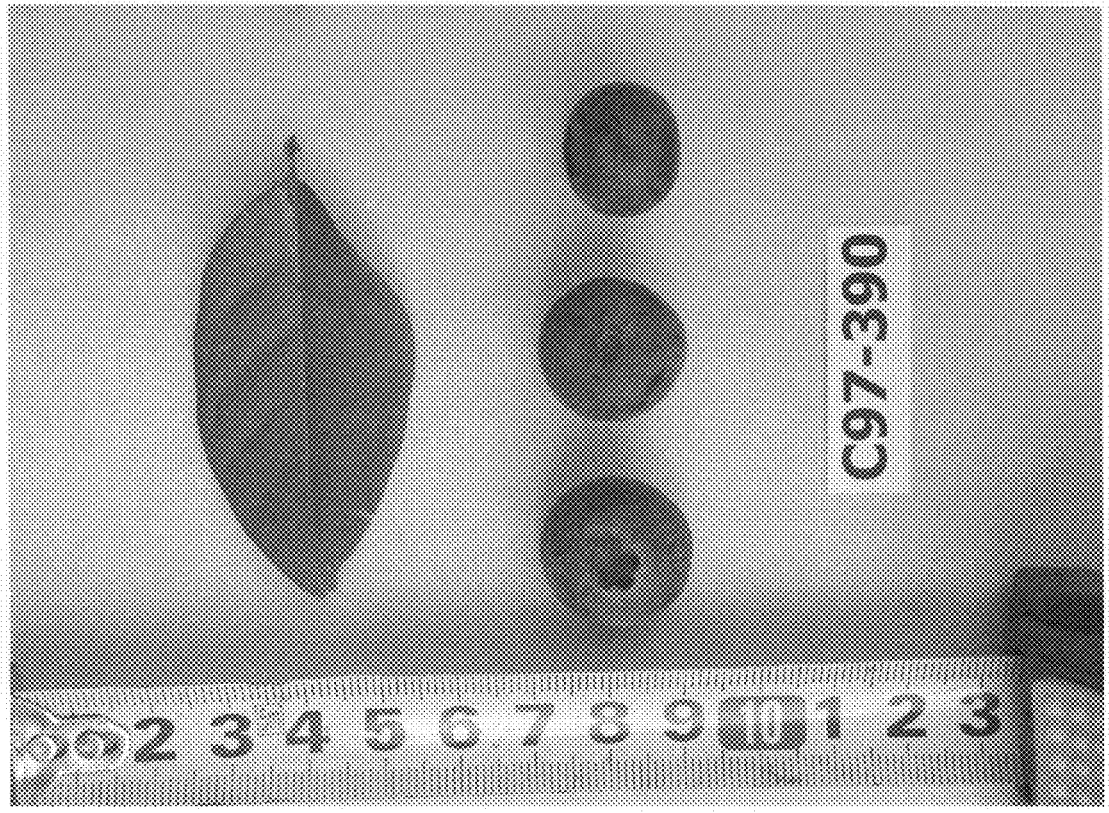
FIG. 2 illustrates a 'C97-390' leaf and berry shapes and dimensions.
Figure 3:
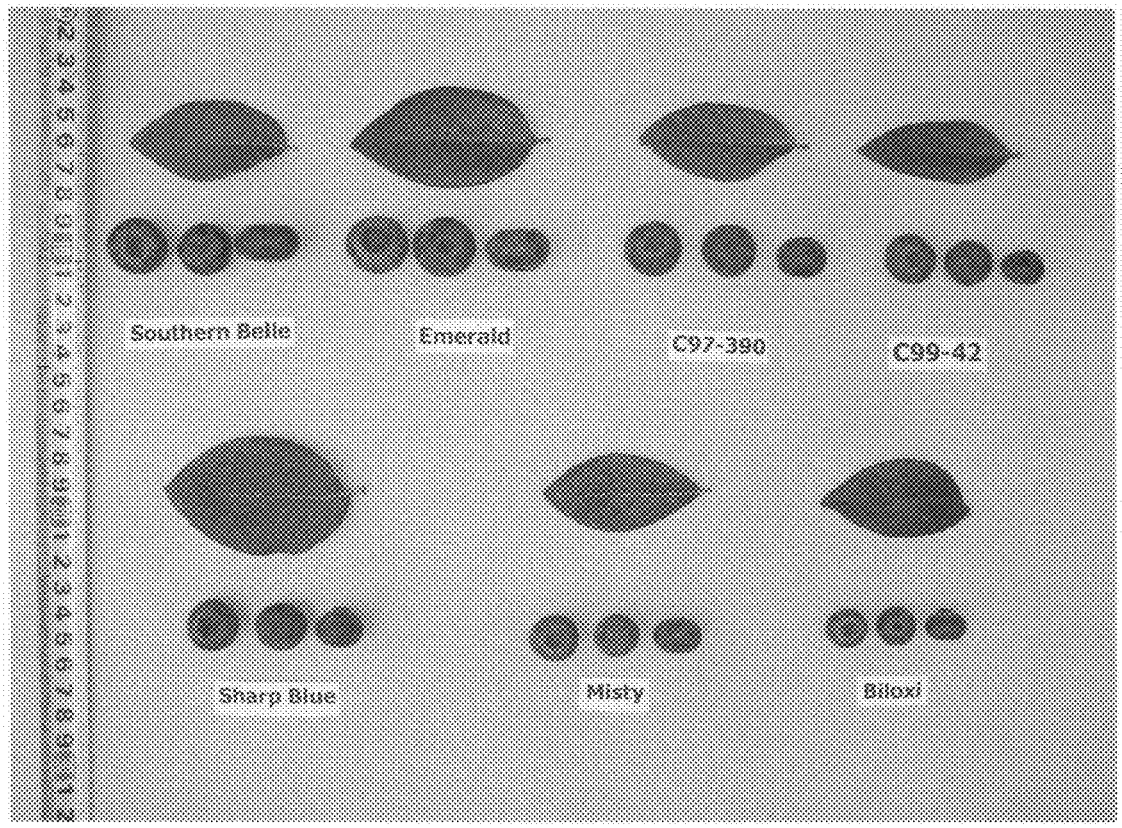
FIG. 3 illustrates a 'C97-390' leaf and berry shapes and dimensions compared to other commercial cultivars.

The following is a detailed botanical description of a new and distinct variety of an *Vaccinium* hybrid ornamental plant known as 'C97-390'. Plant observations were made on plants grown in Corindi Beach, New South Wales, Australia. Unless indicated otherwise, the descriptions disclosed herein are based upon observations made from August to September 2007 of mature 'C97-390' plants (age 4 years) grown in outdoor field plantings with day temperature ranging from 21° C. to 23° C., night temperatures ranging from 10° C. to 12° C., and light levels ranging from 6 to 8 klux. Those skilled in the art will appreciate that certain characteristics will vary with older or, conversely, younger plants. 'C97-390' has not been observed under all possible environmental conditions. Where dimensions, sizes, colors and other characteristics are given, it is to be understood that such characteristics are approximations or averages set forth as accurately as practicable. The phenotype of the variety may vary with variations in the environment such as season, temperature, light quality, light intensity, day length, cultural conditions and the like. Color notations are based on The Royal Horticultural Society Colour Chart, of The Royal Horticultural Society, London, 1995 edition.

Botanical classification: *Vaccinium* hybrid cultivar 'C97-390'.

Parentage:

*Parents.*—Seed parent 'F92-84' (unpatented) and pollen parent 'F 95-54' (unpatented).

Plant:

*Growth habit.*—Plants are upright to bushy. Growth vigor is strong. Plant height is 1.9 m. Plant width is 1.2 m. Flower bud density is medium. Twigginess is low. Time of beginning of leaf bud burst is late (mid to late September) when grown as an evergreen in Australia. Time of beginning of flowering is very early to early (begins early May; peaks mid July) when grown as an evergreen in Australia. Time of fruit ripening is very early to early (begins mid June; peaks mid September) when grown as an evergreen in Australia.

Stem:

*Suckering tendency.*—Plants typically have 5–7 major canes per plant from a base 30 cm in diameter on 6 year old plants.

*Canes.*—Erect to semi-erect with moderate branching; color greyed orange 198C; 2 year old cane diameter 12 mm, colored greyed orange 177B, some flaking of bark, current season wood diameter 3–4 mm, colored yellow green 144C Internode length on strong, new shoots 15–20 mm.

*Fruiting wood.*—Numerous twigs to 10 cm in length.

*Surface texture of new wood.*—Smooth.

*Fully developed leaf.*—Length medium 60–70 mm Width medium approximately 25–30 mm Shape elliptic Color yellow green 137A Intensity of color medium Margin entire Undulation of margin weak Pubescence of upper side absent Pubescence of lower side absent Cross sectional profile flat Longitudinal profile straight Attitude broad acute to horizontal.

*Inflorescence.*—Length of peduncle to 12 mm Length of pedicel long 4–6 mm Number of flowers per cluster median 7 Flower cluster density is medium.

*Flowers.*—Length of corolla tube short-medium (to 13 mm) Width of corolla tube narrow-medium (to 9 mm) Corolla aperture diameter 3 mm Color of corolla white 155D Anthocyanin coloration of corolla absent Corolla ridges present Protrusion of stigma present Fragrance weak Shape urceolate Abundance of pollen high Calyx (with sepals) diameter 5–6 mm Calyx color green 138A.

Productivity: 3 to 4 kg per season from 3–4 year old plants planted at 3.0 m×0.9 m density.

Cold hardiness: 'C97-390' has not been grown in all environments including harsh winter environments. Cold tolerance is expected to be low. Plants have survived winter freeze in Australia to minus 8° C. with minimal winter dieback of young shoots and resultant loss of fruit and flowers, poor growth vigor.

Chilling requirement: 'C97-390' has not been grown in all environments and is typically grown as an evergreen crop where chilling hours are not important. 'C97-390' is classed as 'low chill', typical of Southern Highbush Blueberry varieties with an estimated chilling requirement of 250 hours (not tested).

Leafing: Plants retain leaves year round (at Corindi beach, NSW Australia) and 'C97-390' is grown commercially as an evergreen crop. New leafing occurs in mid to late September at Corindi beach, NSW Australia.

*Fruit.*—Unripe fruit color intensity light Unripe fruit color 144A Cluster density is medium Diameter is medium (mean 17.9 mm) Weight medium (approximately 2.4 g) Shape globose Attitude of calyx erect Diameter of calyx basin medium (mean 7 mm) Depth of calyx basin is shallow (to 1 mm) Intensity of bloom weak to medium Intensity of blue color of skin with bloom removed is very dark Color of skin 202A Sweetness when ripe medium Firmness when ripe medium Acidity when ripe weak to medium Size of scar is small (1.0–1.5 mm) Storage quality good.

Date of 50% maturity: Approximately 5$^{th}$ September at Corindi beach, NSW Australia.

Fruit development period: Approximately 55 days in protected cultivation at Corindi beach, NSW Australia.

*Seed.*—Seed color greyed orange 165B Seed abundance in fruit medium Seed size 1.6–1.8 mm long for fully developed seeds.

Tolerance to disease: 'C97-390' has shown moderate resistance to root disease (*phytophthora* spp) and good resistance to blueberry rust compared to commercial varieties 'Sharpe Blue' and 'Emerald'. Also demonstrates moderate to low resistance to the fruit disease Anthracnose (*Colletotrichum gleosporoides*).

What is claimed is:

1. A new and distinct cultivar of blueberry plant named 'C97-390', substantially as herein shown and described.

* * * * *

UNITED STATES PATENT AND TRADEMARK OFFICE
Certificate

Patent No. PP. 20,642 B2 Patented: January 12, 2010

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Gary Wright, Corindi Beach (AU); and Paul Lyrene, Micanopy, FL (US).

Signed and Sealed this Ninth Day of April 2013.

SHUBO (JOE) ZHOU
*Supervisory Patent Examiner*
Art Unit 1661/1638
Technology Center 1600